(12) United States Patent
Haider

(10) Patent No.: US 6,740,089 B2
(45) Date of Patent: May 25, 2004

(54) ORTHOPEDIC HOOK SYSTEM

(76) Inventor: Thomas T. Haider, 2357 Knob Hill Dr., Riverside, CA (US) 92506

( * ) Notice: Subject to any disclaimer, the term of this patent is extended or adjusted under 35 U.S.C. 154(b) by 0 days.

(21) Appl. No.: 10/043,555

(22) Filed: Jan. 10, 2002

(65) Prior Publication Data

US 2003/0130659 A1 Jul. 10, 2003

(51) Int. Cl.⁷ ............................................. A61B 17/84
(52) U.S. Cl. ............................ 606/72; 606/61; 606/60
(58) Field of Search ............................ 606/61, 73, 71, 606/70, 72, 151

(56) References Cited

U.S. PATENT DOCUMENTS

| | | |
|---|---|---|
| 4,411,259 A | 10/1983 | Drummond |
| 5,688,273 A * | 11/1997 | Errico et al. ............ 606/61 |
| 5,863,293 A | 1/1999 | Richelsoph |
| 5,964,760 A | 10/1999 | Richelsoph |
| 6,077,262 A * | 6/2000 | Schlapfer et al. ........ 606/61 |
| 6,083,226 A | 7/2000 | Fiz |
| 6,117,136 A | 9/2000 | Von Strempel |
| 6,132,432 A | 10/2000 | Richelsoph |
| 6,179,838 B1 | 1/2001 | Fiz |
| 6,475,218 B2 * | 11/2002 | Gournay et al. ........ 606/61 |

* cited by examiner

Primary Examiner—Cary E. O'Connor
Assistant Examiner—Candice Melson
(74) Attorney, Agent, or Firm—Harold L. Jackson

(57) ABSTRACT

A orthopedic hook system for use with a rod in correcting scoliosis comprising a body with a hook section and a rod engaging section, a grasp screw, a cap, and a set screw. The hook section fits over the bone and the grasp screw is used to secure the bone in place. The rod is brought within the rod receiving section and the cap is placed over the U-shaped rod receiving section. The set screw is used to force the cap into contact with the rod. The rod is thereby secured in place between the rod receiving section and the cap. Any excess length of the U-shaped rod is then removed.

8 Claims, 3 Drawing Sheets

ORTHOPEDIC HOOK SYSTEM

BACKGROUND OF THE INVENTION

1. Field of the Invention

This invention relates to an orthopedic hook system for use in correcting scoliosis.

2. Description of the Prior Art

Scoliosis is a medical term that denotes an abnormal curvature of the spine. This abnormality usually occurs as a single primary curvature or as primary curvature accompanied by a compensating secondary curvature.

Where the spine is curved from side-to-side, the condition is known as nonstructural scoliosis. If the spine is not only curved but also twisted, the condition is known as structural scoliosis.

There are varying degrees of scoliosis ranging from where the condition is hardly visible to where the deviation of the natural curvature can have an adverse impact on a person's lung capacity, personal appearance, and ability to engage in physical activities. This is in addition to the emotional and psychological impact a person may suffer due to the disfiguring nature of the condition.

One method of correcting this condition is to surgically install a series of rods and supporting devices to reconfigure the spine to approximate a more normal curvature. In this process, a number of supporting devices incorporate a hook that comes into contact with the bones of the spine.

U.S. Pat. Nos. 4,411,259 to Drummond (the '259 patent), 5,863,293 to Richelsoph (the '293 patent), 5,964,760 to Richelsoph (the '760 patent), 6,083,226 to Fiz (the '226 patent), 6,117,136 to Von Strempel (the '136 patent), 6,132,432 to Richelsoph (the '432 patent) and 6,179,838 to Fiz (the '838 patent) all disclose a hook as part of a bone fixation device for use with a series of rods to secure the spine, or regions of the spine, in a particular position. In each case identified, the hook is placed into contact with an element of the bone such as the laminar part of the vertebra. The hook remains in place due to the forces created by the system of fixation devices, rods, and to some degree the force of the spine in opposition to the corrective measures.

Since the hooks in the aforementioned patents do not clamp against the bone to remain in place when initially installed, the hooks are movable when first put into place. This can cause problems when a hook slips, or moves, into a position that is not desirable while the remaining hooks and rods are being secured into place. Not only is it time consuming to correct the positioning of the hook, but due to the location of the instruments about the spinal column there is an increased risk of problems arising due to improper movement of the hook.

Another problem arises in securing the rod to the fixation device. Due to the side-to-side and potential twisting movement of the spine found in cases of scoliosis, the fixation devices may not be level in relation to one another at the beginning of the operative procedure. Thus the fixation device must have a rod engaging element that is long enough to capture the rod when the rod is at a greater distance from the fixation device.

The '432, '760, and '293 patents all disclose a rod receiving mechanism that has two arms that are designed to encompass the rod and aid in directing the rod toward a seat thereby securing the rod in place. Naturally, these devices could be manufactured with very long arms to capture a rod at almost any practical distance from the fixation device. However, this creates another problem.

When the rod is finally secured into position, the portion of the arms that are not operating with the locking ring or set screw may be so long that it creates complications. This excess threaded metal surface is not desirable in the area of the spine. Furthermore, the distance between the bones of the spine and the surface of the skin on a patients back is not very great. The arms must be short enough to be completely covered by the patient's flesh when the operation is complete.

What is needed is a hook that can be secured in place while performing the scoliosis correcting procedure and arms that are long enough to engage the rod and yet can be reduced in length when the rod is in place so that there is little if any excess threaded metal beyond the securing cap or screw.

SUMMARY OF THE INVENTION

The invention is directed to an orthopedic hook system comprising a hook shaped clamping section being substantially saddle shaped for receiving a bone segment and a rod receiving section, the clamping section has a threaded opening extending through the hook shaped clamping section and an upper side. A grip screw is adapted to work in cooperation with the threaded opening to secure the bone segment in place within the hook shaped clamping section. The rod receiving section is substantially U-shaped and has a threaded inside surface and a base adapted to receive the rod with the rod receiving section extending above the upper side of the hook shaped clamping section. A cap is adapted to fit over the substantially U-shaped rod receiving cavity and has a concave surface for engaging the rod, and a set screw adapted for use with the threaded inside surface of the substantially U-shaped rod receiving section such that the set screw engages the cap, which in turn secures the rod between the cap and the base of the rod receiving section.

DESCRIPTION OF THE PREFERRED EMBODIMENT

Figure 1:
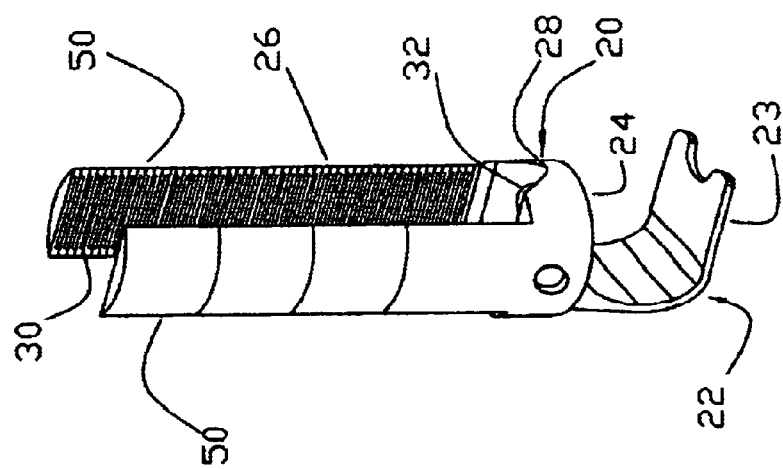
FIG. 1 is a perspective view of the hook body.

The present invention may best be understood by reference to the following description taken in conjunction with the accompanying drawings. Turning now to FIG. 1, the body 20 is comprised of a hook section 22 and a rod receiving section 26. The hook section 22 is comprised of a hook 23 having an upper side 24. The hook 23 fits over a bone segment.

The rod receiving section 26 is substantially U-shaped. That means the two post 50 are opposing one another and the base 28 is between the post 50. The base 28 is attached to the upper side 24 of the hook 23 and the base 28 is adapted to receive the rod 33.

Figure 2:
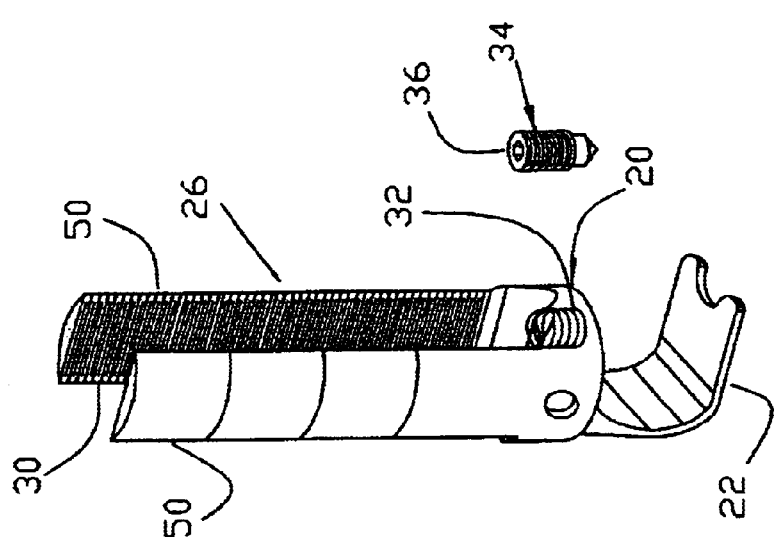
FIG. 2 is a perspective view of the hook body and the grip screw.

FIG. 2 identifies the threaded opening 32 and the grip screw 34. The grip screw 34 has a wrench engaging surface 36 such that the grip screw 34 can be rotatably inserted into the threaded opening 32. When the bone is within the cavity formed by the hook 23, insertion of the grip screw 34 through the threaded opening 32 and into the bone secures the bone in place in relation to the hook 23.

Figure 2A:
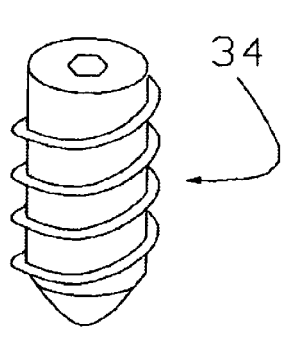
FIG. 2a is a side view of a threaded grip screw.
Figure 2B:
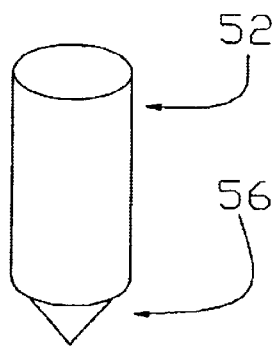
FIG. 2b is a side view of a pin used to grip the bone.
Figure 2C:
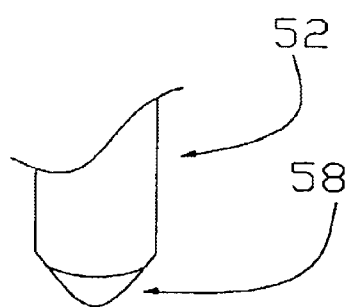
FIG. 2c is a side view of the griping device having a rounded tip.
Figure 2D:
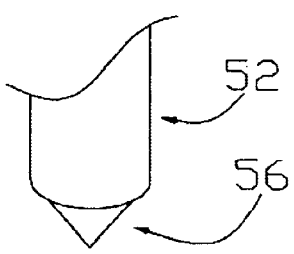
FIG. 2d is a side view of the griping device having a pointed tip.
Figure 2E:
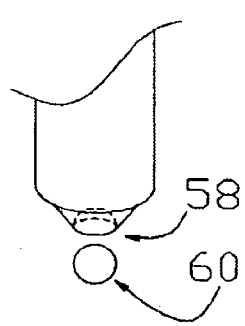
FIG. 2e is a side view of the griping device having a ball at the tip.
Figure 2F:
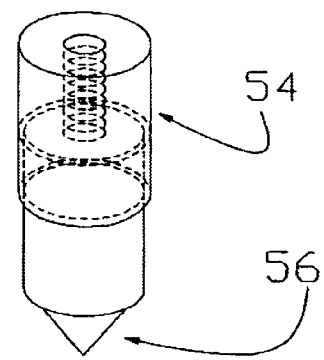
FIG. 2f is a side view of the griping device having a spring.

The griping can be accomplished by numerous means including, but not limited to, the use of a screw such as in FIG. 2a, or a pin as in FIG. 2b, or a spring mounted pin as in FIG. 2f. The tip of the gripping device can be a variety of shapes. A pointed tip 56 tip as in FIG. 2d is suited for securing the hook in place with a limited range of motion. A rounded tip 58 as in FIGS. 2c and 2e can be used where it is desirable to allow for some movement of the device. In FIG. 2e, the rounded tip 58 can be comprised of a separate ball 60 that is attached and freely movable within the pin 52. The degree and direction of movement being determined by such factors as the shape of the surface of the bone that is in contact with the griping device. In FIG. 2f, a spring 54 allows for tension between the pin 52 and the rod 33.

Figure 3:
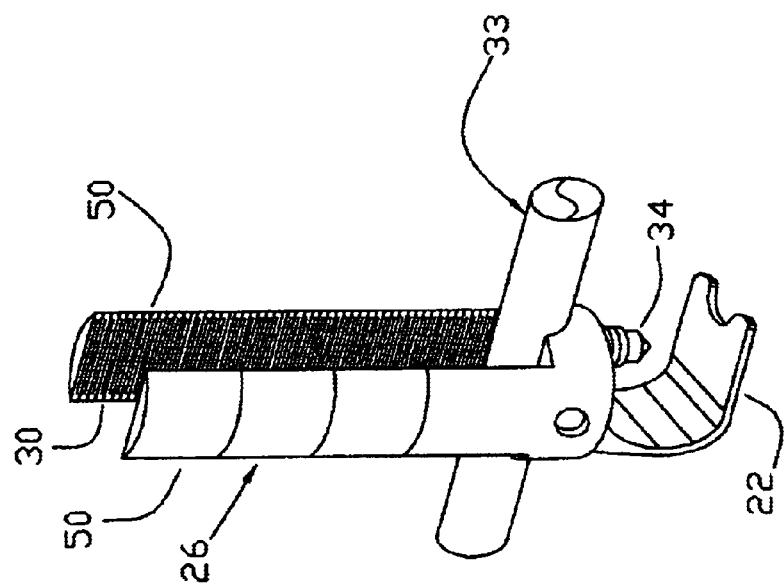
FIG. 3 is a perspective view of the hook body with the rod in place.

In FIG. 3, the grip screw 34 is in place and the rod 33 is in contact with the base 28. It is important to note that when the rod 33 is initially inserted into the rod receiving section 26 the rod 33 may not be in contact with the base 28. It may be necessary to adjust the patient and other equipment so that the rod 33 can be brought into contact with the base 28. This is an advantage to the post 50 being longer.

Figure 4:
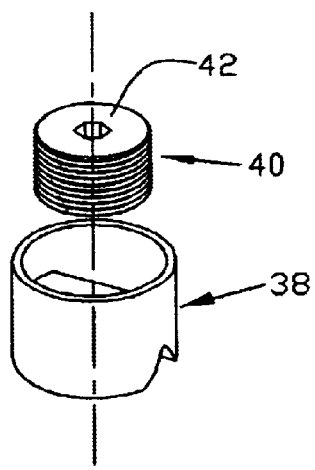
FIG. 4 is a side view of the cap and grip screw.
Figure 4A:
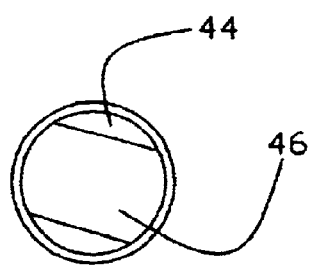
FIG. 4a is a top view of the cap.

FIG. 4 shows the cap 38 and the set screw 40 with the wrench engaging surface 42 of the set screw 40 present. FIG. 4a identifies the opening 44 that is adapted to receive the post 50 so that the cap 38 can be brought into contact with the rod 33.

Figure 5:
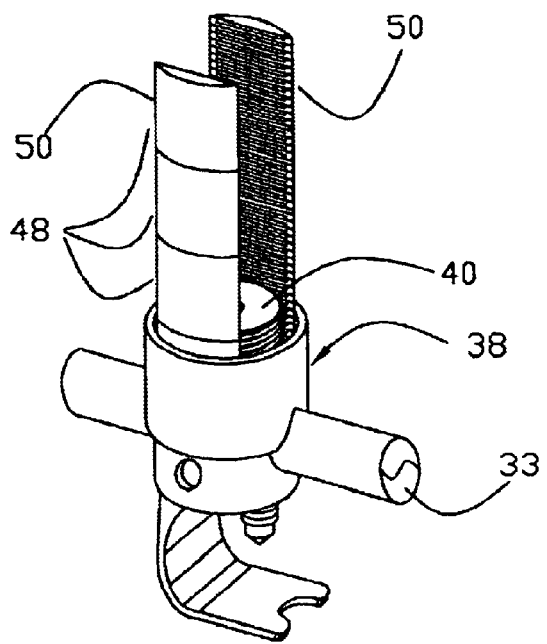
FIG. 5 is a perspective view of the orthopedic hook system with the rod secured in place.

Turning now to FIG. 5, the cap 38 is placed over the rod 33 and brought into contact with the rod 33. The set screw 40 is rotatably inserted between the post 50 and screwed down to come into contact with the cross member 46 of the cap 38. This forces the cap, with its lower concave surface, onto the rod 33 thereby securing the rod 33 in place.

Once the rod 33 is brought into contact with the base 28, a number of the sections of the post 50 are no longer useful. At that time, a number of detachable segments 48 can be removed.

Figure 6:
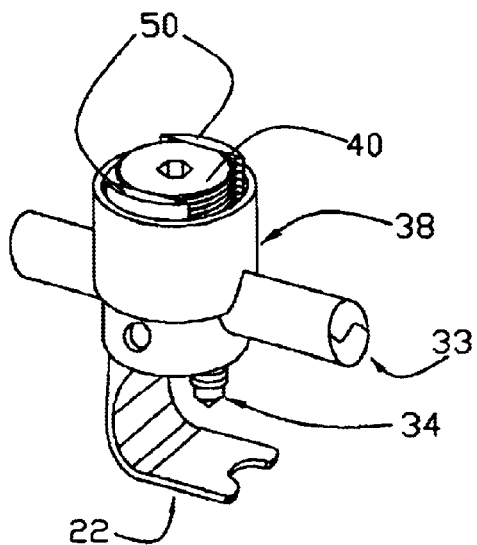
FIG. 6 is a perspective view of the orthopedic hook system with a number of detachable elements removed.

In FIG. 6, a number of detachable segments 48 which have been removed. The number removed is determined by the circumstances of each case, but in general it amounts to the detachable segments 48 that are not in use by the set screw 40. The result is a secure foundation supporting the rod 33 and no excess detachable segments 48.

There has thus been described a novel orthopedic hook system. Modifications of the preferred embodiment may be made without departing from the spirit and scope of the invention as defined in the appended claims. Therefore, it is intended that the drawings be interpreted as illustrative and not in any way viewed as being a limitation on the invention.

What is claimed is:

1. A orthopedic hook system for use with a rod for immobilizing bone segments comprising;

a) a body comprising a hook shaped clamping section and a rod receiving section, the hook shaped clamping section being substantially saddle shaped and having an upper side, a lower side, and a connecting member therewith, the hook shaped clamping section being adapted to receive a bone segment, the rod receiving section extending above the upper side of the hook shaped clamping section and having a substantially U-shaped form having a threaded inside surface and a base being adapted to receive the rod and;

b) a grip screw adapted for use with a threaded opening, the threaded opening extending through the upper side of the hook shaped clamping section the grip screw working in conjunction with the hook shaped clamping section to secure the bone segment within the hook shaped clamping section; and c) a set screw adapted for use with the threaded inside surface of the rod receiving section for engaging the rod between the set screw and the base of the rod receiving section.

2. The orthopedic hook system for use with a rod for immobilizing bone segments of claim 1 further comprising a cap adapted to fit over the rod housing and having a cross member for engaging the rod, wherein set screw engages the cap and secures the rod between the cap cross member and the base of the rod receiving section.

3. The orthopedic hook system for use with a rod for immobilizing bone segments of claim 2 wherein the grip screw has a wrench engaging surface so that the grip screw can be rotatably inserted through the threaded opening, the threaded opening extending through the base of the rod receiving section and the upper side of the hook section and the grip screw being adapted to engage the bone between the opposing sides of the hook section.

4. The orthopedic hook system for use with a rod for immobilizing bone segments of claim 2 wherein the substantially U-shaped form of the rod receiving section is comprised of posts having a plurality of detachable segments.

5. The orthopedic hook system for use with a rod for immobilizing bone segments of claim 2 wherein the set screw further comprises a wrench engaging surface such that the set screw is rotatable within the substantially U-shaped form of the rod receiving section to engage the cap for securing the rod between the cap and the base of the rod receiving section.

6. The orthopedic hook system for use with a rod for immobilizing bone segments of claim 2 wherein the cap further comprises openings adapted to receive the substantially U-shaped form of the rod receiving section and a cross member adapted to engage the rod and the set screw.

7. A method for utilizing a orthopedic hook system and a rod for immobilizing bone segments, the orthopedic hook system having a body comprising a hook shaped clamping section and a rod receiving section, the hook shaped clamping section being substantially saddle shaped and having an upper side adapted to receive a bone segment, the rod receiving section extending above the upper side of the hook shaped clamping section and having a substantially U-shaped form having a threaded inside surface with the base being adapted to receive the rod, and a grip screw adapted for use with a threaded opening, the threaded opening extending through the upper side of the hook shaped clamping section, a cap adapted to fit over the rod housing and having a lower concave surface for engaging the rod, and a set screw adapted for use with the threaded inside surface of the rod receiving section for engaging the cap and securing the rod between the cap and the base of the rod receiving section comprising the steps of;

a) placing the hook over a bone segment;
   b) securing the bone segment in place by rotating the grip screw within the threaded opening so that the grip screw engages the bone segment;
   c) inserting the rod within the substantially U-shaped form of the rod receiving section;
   d) placing the cap over the substantially U-shaped form of the rod receiving section;
   e) inserting the set screw within the substantially U-shaped form of the rod receiving section;
   f) rotating the set screw until the set screw forces the cap into contact with the rod and thereby secured the rod in place; and
   g) detaching segments of the post that do not engage the set screw.

8. A orthopedic hook system for use with a rod for immobilizing bone segments comprising;

a) a body comprising a hook shaped clamping section and a rod receiving section, the hook shaped clamping section being substantially saddle shaped and having an upper side, a lower side, and a connecting member therewith, the hook shaped clamping section being adapted to receive a bone segment, the rod receiving section extending above the upper side of the hook shaped clamping section and having a pair of spaced posts in a substantially U-shaped form with the posts having a threaded inside surface and the base being adapted to receive the rod and;
   b) manually operable griping means for securing a bone segment within the hook shaped clamping section;
   c) a cap adapted to fit over the rod housing and having a cross member for engaging the rod; and
   d) a set screw adapted for use with the threaded posts for engaging the cap and securing the rod between the cap and the base of the rod receiving section.

* * * * *